(12) United States Patent
Fridman et al.

(10) Patent No.: US 7,835,804 B2
(45) Date of Patent: Nov. 16, 2010

(54) REMOVING ARTIFACT IN EVOKED COMPOUND ACTION POTENTIAL RECORDINGS IN NEURAL STIMULATORS

(75) Inventors: Gene Yevgeny Fridman, Santa Clarita, CA (US); Rankiri Tissa Karunasiri, Castaic, CA (US)

(73) Assignee: Advanced Bionics, LLC, Valencia, CA (US)

( * ) Notice: Subject to any disclaimer, the term of this patent is extended or adjusted under 35 U.S.C. 154(b) by 872 days.

(21) Appl. No.: 11/734,233

(22) Filed: Apr. 11, 2007

(65) Prior Publication Data

US 2007/0244410 A1    Oct. 18, 2007

Related U.S. Application Data

(60) Provisional application No. 60/745,021, filed on Apr. 18, 2006.

(51) Int. Cl.
*A61N 1/05* (2006.01)
(52) U.S. Cl. .......................................... 607/137; 607/56
(58) Field of Classification Search ..................... 607/2, 607/55, 56, 115, 136, 137
See application file for complete search history.

(56) References Cited

U.S. PATENT DOCUMENTS

| | | | |
|---|---|---|---|
| 5,531,774 A | 7/1996 | Schulman et al. |
| 5,833,714 A | 11/1998 | Loeb |
| 6,157,861 A | 12/2000 | Faltys et al. |
| 6,195,585 B1 | 2/2001 | Karunasiri et al. |
| 6,496,734 B1 | 12/2002 | Money |
| 6,594,525 B1 | 7/2003 | Zierhofer |
| 7,171,261 B1 | 1/2007 | Litvak et al. |

(Continued)

FOREIGN PATENT DOCUMENTS

WO    WO 01/06810 A2    1/2001

(Continued)

OTHER PUBLICATIONS

Loizou, P.C., Mimicking the human ear. Ieee Signal Processing Magazine, Sep. 1998. 15(5): p. 101-130.

(Continued)

*Primary Examiner*—Carl H Layno
*Assistant Examiner*—Brian T Gedeon
(74) *Attorney, Agent, or Firm*—Victoria Aguilera Poissant; Bryant R. Gold

(57) ABSTRACT

The accuracy of neural response recordings in neural stimulators, e.g., cochlear implants, is often degraded by a recording artifact. An idealized electrical-equivalent model of a neural stimulator is created to study, measure and compensate for artifact evoked compound action potential (eCAP). Using this model, the artifact is shown to occur even when the electrical components that make-up the neural stimulator are ideal. The model contains parasitic capacitances between the electrode wires. The model demonstrates that these small parasitic capacitances provide a current path during stimulation which can deposit charge on the electrode-tissue interfaces of the recording electrodes. The dissipation of this residual charge and the charge stored across the stimulating electrode is seen as the recording artifact. The proposed solution for eliminating the artifact problem is realized by utilizing a capacitive electrode material, e.g., $TiO_2$, $Ta_2O_5$, or other dielectric coatings or films, instead of Faradaic electrode material, e.g., Platinum (Pt), Pt—Ir alloy or similar alloys, on the neural stimulator electrode lead.

12 Claims, 13 Drawing Sheets

U.S. PATENT DOCUMENTS

| | | | |
|---|---|---|---|
| 7,203,548 | B2 | 4/2007 | Whitehurst et al. |
| 7,206,640 | B1 | 4/2007 | Overstreet |
| 7,359,752 | B1 * | 4/2008 | Bornzin et al. ............... 607/27 |
| 2005/0101878 | A1 | 5/2005 | Daly et al. |

FOREIGN PATENT DOCUMENTS

| | | |
|---|---|---|
| WO | WO 01/13991 A1 | 3/2001 |
| WO | WO 02/082982 A1 | 10/2002 |

OTHER PUBLICATIONS

Rauschecker, J.P. and R.V. Shannon, Sending sound to the brain. Science, Feb. 8, 2002. 295(5557): p. 1025-1029.

Miller, C.A., et al., Electrically evoked compound action potentials of guinea pig and cat: responses to monopolar, monophasic stimulation. Hearing Research, Mar. 2, 1998. 119(1-2): p. 142-154.

Cohen, L.T., et al., Spatial spread of neural excitation in cochlear implant recipients: comparison of improved ECAP method and psychophysical forward masking. Hearing Research, Mar. 11, 2003. 179(1-2): p. 72-87.

Miller, C.A., et al., Intracochlear and extracochlear ECAPs suggest antidromic action potentials. Hearing Research, Sep. 11, 2004. 198(1-2): p. 75-86.

Klop, W.M.C., et al., A new method for dealing with the stimulus artefact in electrically evoked compound action potential measurements. Acta Oto-Laryngologica, 2004. 124(2): p. 137-143.

Brown, C.J. and P.J. Abbas, Electrically Evoked Whole-Nerve Action-Potentials—Parametric Data from the Cat. Journal of the Acoustical Society of America, Nov. 1990. 88(5): p. 2205-2210.

Brown, C.J. and P.J. Abbas, Electrically Evoked Whole-Nerve Action-Potentials: Data from Human Cochlear Implant Users. Journal of the Acoustical Society of America, Sep. 1990. 88(3): p. 1385-1391.

Abbas, P.J., et al., Summary of results using the nucleus CI24M implant to record the electrically evoked compound action potential. Ear and Hearing, Feb. 1999. 20(1): p. 45-59.

Briaire, J.J. and J.H.M. Frijns, Unraveling the electrically evoked compound action potential. Hearing Research, Apr. 27, 2005. 205(1-2): p. 143-156.

McAdams, E.T., et al., The Linear and Nonlinear Electrical-Properties of the Electrode-Electrolyte Interface. Biosensors & Bioelectronics, 1995. 10(1-2): p. 67-74.

Vanpoucke, F.J., A.J. Zarowski, and S.A. Peeters, Identification of the impedance model of an implanted cochlear prosthesis from intracochlear potential measurements. Ieee Transactions on Biomedical Engineering, Dec. 2004. 51 (12): p. 2174-2183.

Rose, T.L., E.M. Kelliher, and L.S. Robblee, Assessment of Capacitor Electrodes for Intracortical Neural Stimulation. Journal of Neuroscience Methods, 1985. 12(3): p. 181-193.

Loeb, G.E., et al., Injectable Microstimulator for Functional Electrical-Stimulation. Medical & Biological Engineering & Computing, 1991. 29(6): p. NS13-NS19.

Janders M., E.U., Stelzle M., Nisch W. Novel Thin Film Titanium Nitride Midro-Electrode With Excellent Charge Transfer Capability for Cell Stimulation and Sensing Applications. in 18th Annual International Conference of the IEEE Engineering in Medicine and Biology Society. 1996. Amsterdam.

* cited by examiner

| Parameter Name | Parameter Description | Range of Relevant Values | Nominal Values |
|---|---|---|---|
| Cc1 | Coupling capacitor for stimulating electrode | 0.1 μF | 0.1 μF |
| Cc2 | Coupling capacitor for recording electrode | 0.1 μF | 0.1 μF |
| Cc3 | Coupling capacitor for recording return electrode | 0.1 μF | 0.1 μF |
| Csg | Parasitic capacitance between stimulating electrode wire and recording return electrode | 4 to 10 pF | 6 pF |
| Crg | Parasitic capacitance between recording electrode wire and recording return electrode | 4 to 10 pF | 6 pF |
| Csr | Parasitic capacitance between stimulating electrode wire and recording electrode wire | 6 to 30 pF | 15 pF |
| Cs | Stimulating electrode interface Warburg capacitance | 2 to 10 nF | 6 nF |
| Rs | Stimulating electrode interface Faradaic resistance | 7 to 30 kΩ | 18.5 kΩ |
| Cr | Recording electrode interface Warburg capacitance | 2 to 10 nF | 6 nF |
| Rr | Recording electrode interface Faradaic resistance | 7 to 30 kΩ | 18.5 kΩ |
| Eg (capacitor) | Recording return electrode interface Warburg capacitance | 56 to 280 nF | 168 nF |
| Eg (resistor) | Recording return electrode interface Faradaic resistance | 25 to 1.5 kΩ | 8 kΩ |
| Esret (capacitor) | Stimulation return electrode interface Warburg capacitance | 2 to 2 μF | 1.1 μF |
| Esret (resistor) | Stimulation return electrode interface Faradaic resistance | 70 to 400 Ω | 235 Ω |
| RsAccess | Access resistance for stimulation electrode | 4 to 10 kΩ | 7 kΩ |
| RrAccess | Access resistance for recording electrode | 4 to 10 kΩ | 7 kΩ |
| RgAccess | Access resistance for recording return electrode | 4 to 10 kΩ | 7 kΩ |
| RsretAccess | Access resistance for stimulation return electrode | 4 to 10 kΩ | 7 kΩ |
| Rl1 | Longitudinal tissue impedance | 50 to 400 Ω | 150 Ω |
| Rl2 | Longitudinal tissue impedance (recording return to electrode with recording return outside the cochlea) | 5 to 40 kΩ | 22.5 kΩ |
| Rl3 | Longitudinal tissue impedance (recording return to stimulation return) | 50 to 400 Ω | 150 Ω |
| Rt1 | Transverse impedance | 2 to 30 kΩ | 15 kΩ |
| Rt2 | Transverse impedance | 2 to 30 kΩ | 15 kΩ |
| Rt3 | Transverse impedance | 2 to 30 kΩ | 15 kΩ |
| Rt4 | Transverse impedance | 2 to 30 kΩ | 15 kΩ |

FIG. 4

REMOVING ARTIFACT IN EVOKED COMPOUND ACTION POTENTIAL RECORDINGS IN NEURAL STIMULATORS

The present application claims the benefit of U.S. Provisional Patent Application Ser. No. 60/745,021, filed Apr. 18, 2006.

BACKGROUND OF THE INVENTION

The present disclosure relates to implantable medical devices, and more particularly implantable medical devices that stimulate the neural system, e.g. cochlear stimulators (referred to hereafter as a "neural stimulator" or simply as a "stimulator"). Even more particularly, the disclosure relates to a neural stimulator electrical model that measures evoked compound action potential (eCAP) artifact, and further to systems and methods for eliminating a slow decaying artifact in the eCAP recordings in order to increase the accuracy of the eCAP measurements.

In an implantable medical device, particularly an implantable neural stimulator, there is a need to measure internal voltages, determine electrode impedances, determine output stimulus linearity, sense and measure biological responses to an electrical impulse, as well as to monitor and measure other biological activities that are associated with or occur coincident with the operation of the device.

For example, in order to measure a biological response to an applied stimulus (i.e., an "evoked response"), there is a need to deal with the presence of the stimulus artifacts which accompany any applied stimulus. Having the capability of sensing and monitoring the evoked response to an applied stimulus provides a very valuable tool for setting the stimulus parameters at an appropriate level for a given patient. However, sensing the evoked response has been difficult since it is such a small signal compared to the stimulus artifact.

Profound deafness due to sensorineuronal hearing loss can be alleviated with varying degrees of success, using a neural stimulator known as a cochlear implant (CI) prosthetic. This device includes both external (non-implanted) and implanted portions. The implanted portion comprises an implantable cochlear stimulator integrally attached to a cochlear electrode lead. The implanted cochlear stimulator is affixed to the temporal bone during surgery, and the electrode lead is positioned in the cochlea along the basilar membrane. The electrode lead includes, at its distal end, a multiplicity, e.g., sixteen, spaced-apart electrodes that may be inserted into a human cochlea, any one of which may be activated for application of an electrical stimulus to cochlear tissue. The electrodes are stimulated in a tonatopic manner to elicit a response in the auditory nerve.

The modern cochlear implants contain amplification and digitization circuitry which is sufficiently accurate to allow monitoring of the auditory nerve response evoked by a stimulus pulse. These evoked compound action potentials (eCAPs) are used in research settings to study the pathology of hearing loss and benefits of cochlear implants. These measurements are also commonly recorded in the clinical setting in order to determine the proper parameters for fitting the CI to benefit a particular patient. Evoked compound action potentials measurements are also known as neural response imaging (NRI) and neural response telemetry (NRT). (NRI-measurements are described, e.g., in U.S. Pat. Nos. 6,157,861 and 6,195,585, incorporated herein by reference, and relate, in general, to monitoring a response evoked by application of a stimulus pulse.)

An evoked compound action potential occurs at approximately 200 µs after the beginning of the stimulation pulse. The neural signals recorded in this manner have typical amplitudes of 100 to 1000 µV. Evoked compound action potential measurements are often seen superimposed on a decaying artifact. As Klop et al. point out, this artifact has been observed to follow a double exponential [Klop, W. M. C., et al., "*A new method for dealing with the stimulus artefact in electrically evoked compound action potential measurements*". Acta Oto-Laryngologica, 2004. 124(2): p. 137-143.] and approach steady state as either positive or the negative decaying transient. The time constant of the artifact is on the order of tens of microseconds and the amplitude at 200 µs after pulse presentation can be as large as several hundred microvolts. The artifact scales with amplitude of the stimulation pulse. It is consistent for a given recording and so cannot be removed by multiple measurements. This artifact appears unpredictable with regard to electrode impedances, or which electrodes are used for the recording. The nature of the artifact has not been satisfactorily explained.

A number of methods have been developed to remove the artifact from the eCAP recordings. Some of these methods attempt to eliminate the artifact by characterizing the measurement response with the artifact and subtracting the measurement of the artifact alone. These methods are the alternating polarity (AP) recording protocol [Brown, C. J. and P. J. Abbas, "*Electrically Evoked Whole-Nerve Action-Potentials—Parametric Data from the Cat*". Journal of the Acoustical Society of America, 1990. 88(5): p. 2205-2210.], masker-probe (MP) protocol [Abbas, P. J., et al., "*Summary of results using the nucleus CI24M implant to record the electrically evoked compound action potential*". Ear and Hearing, 1999. 20(1): p. 45-59], and the template protocol [Miller, C. A., et al., "*Electrically evoked compound action potentials of guinea pig and cat: responses to monopolar, monophasic stimulation*". Hearing Research, 1998. 119(1-2): p. 142-154.]. Other methods attempt to predict the double exponential model of the artifact and subtract it from the recording [Klop et al., p. 137-143.]

It is thus seen that there is a need for a system and method that eliminates artifact in eCAP recordings in order to speed up the acquisition and increase the accuracy of eCAP measurements, particularly to (1) detect the artifact (2) eliminate the artifact, and (3) maintain the accuracy of neural response recordings in neural stimulators, e.g., cochlear implants.

SUMMARY OF THE INVENTION

The present specification addresses the above and other needs by providing an electrical model that simulates a neural stimulator, e.g., cochlear implant. The model is used to study the accuracy of neural response measurements, e.g., evoked compound action potential (eCAP), and the artifact associated with such response. The findings from the study further improve the accuracy of neural responses in neural stimulators by replacing the electrode materials from the more Faradaic, e.g., Platinum (Pt), Pt—Ir alloy or similar alloys, to more capacitive materials, e.g., Tantalum Pentoxide ($Ta_2O_5$), Titanium Oxide ($TiO_2$), or other dielectric coatings or films, e.g., Titanium Nitride (TiN), Barium Titanate ($BaTiO_3$) or similar coatings, in the electrode lead.

That is, in one aspect, the present disclosure provides a system for measuring the eCAP artifact recordings. The system includes an electrical model that is configured to simulate a neural stimulator. The electrical model is configured to measure eCAP artifact from the simulated electrical neural stimulator.

In accordance with one aspect of the present disclosure, there is provided an electrical-equivalent model configured to measure eCAP artifact. The measurements are recorded using a recording scope which is part of the model. The model includes several electrical components simulating portions of a neural stimulator. The portions include an implant stimulator portion, where the implant stimulator portion includes an ideal current source; an electrode lead portion; an electrode interface portion; and a tissue interface portion. The portions are coupled together to make up the electrical-equivalent model. The model simulates a biphasic current pulse from the ideal current source and the eCAP artifact is measured with the recording scope.

In accordance with another aspect of the present disclosure, the electrode lead portion is modeled with the cross-wire parasitic capacitors. The electrode interface portion is modeled in form of parallel capacitor-resistor pair in series with access resistors. The tissue interface portion is modeled as a resistive-ladder network.

It is a further feature of the present disclosure to use the electrical-equivalent model to measure artifact in evoked compound action potential by simulating a biphasic current pulse, e.g., a biphasic current pulse having approximately a 32 µs/phase duration and a 300 µA/phase amplitude. After the end of the biphasic pulse, the current source is left as an open circuit during a response time.

It is an additional feature of the present disclosure to provide a method of removing an artifact from eCAP measurements. The method includes using the electrical-equivalent model with selected resistance and capacitive values from a capacitive material, e.g., $Ta_2O_5$, $TiO_2$, or similar compounds, or other dielectric coatings or films, e.g., TiN, $BaTiO_3$, or similar coatings or films. With such model, the overall size and amplitude of the artifact can be predicted with good accuracy. Such prediction may then be used as a basis for removing the artifact(s) from the measured eCAP signal.

BRIEF DESCRIPTION OF THE DRAWINGS

The above and other aspects, features and advantages of the present disclosure will be more apparent from the following more particular description thereof, presented in conjunction with the following drawings wherein:

FIG. 4 is a table which shows the ranges of relevant values and nominal values from various cochlear implant measurements previously attained from cochlear implant users;

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

Figure 3:
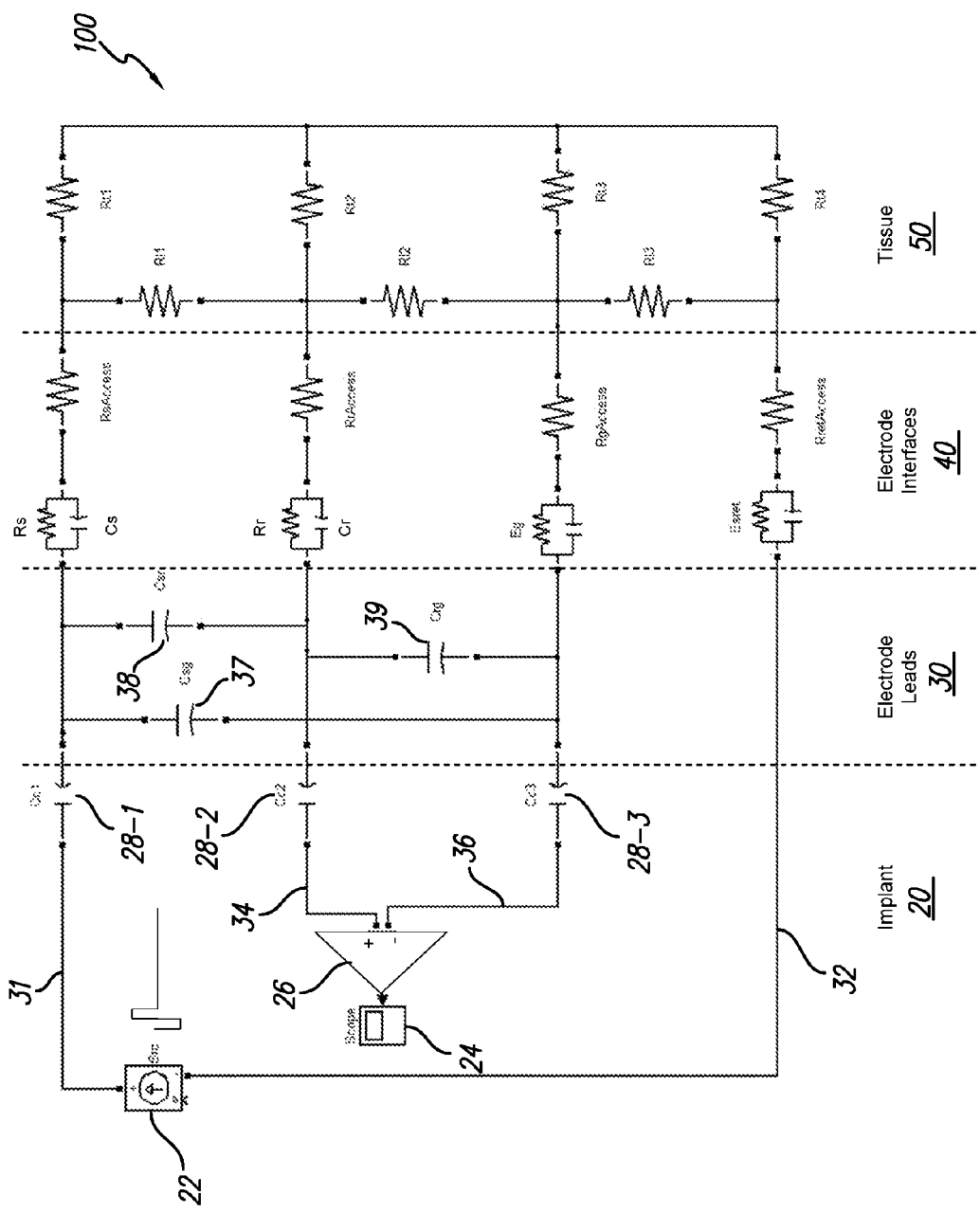
FIG. 3 is one embodiment of an electrical-equivalent model simulating a neural stimulator, e.g., cochlear implant, used to measure eCAP recordings.

In the present disclosure, the probable nature of the described artifact found in eCAP recordings from a neural stimulator, e.g., cochlear implant, is demonstrated by using an electrical-equivalent model 100 shown in FIG. 3. The model 100 includes simplified neural stimulation portion modeled with ideal hardware components in conjunction with electrode-tissue interfaces. Using model 100 the artifact which matches the typical characteristics of the recorded artifacts can be produced. This artifact exists even when the ideal current sources and ideal recording hardware components are used to obtain the measurement. The artifact appears as the result of dissipating of the residual charges stored at the stimulating and the recording electrode immediately following the stimulation pulse. During the stimulation phase of eCAP recording, some of the current leaks through the parasitic capacitance between the electrode wires and charges the recording electrode interface. Then, following the stimulation phase of the recording, the charge stored at the recording and stimulating electrode interfaces discharge. This discharge is seen as the artifact by the recording hardware. Finally, the solution for eliminating this artifact can be obtained by using pure capacitive electrode materials, e.g., $Ta_2O_5$, $TiO_2$, or other dielectric coatings or films, in place of the standard Faradaic electrode materials, e.g., Pt, Pt—Ir or similar alloys, as will be explained hereinafter.

Figure 1:
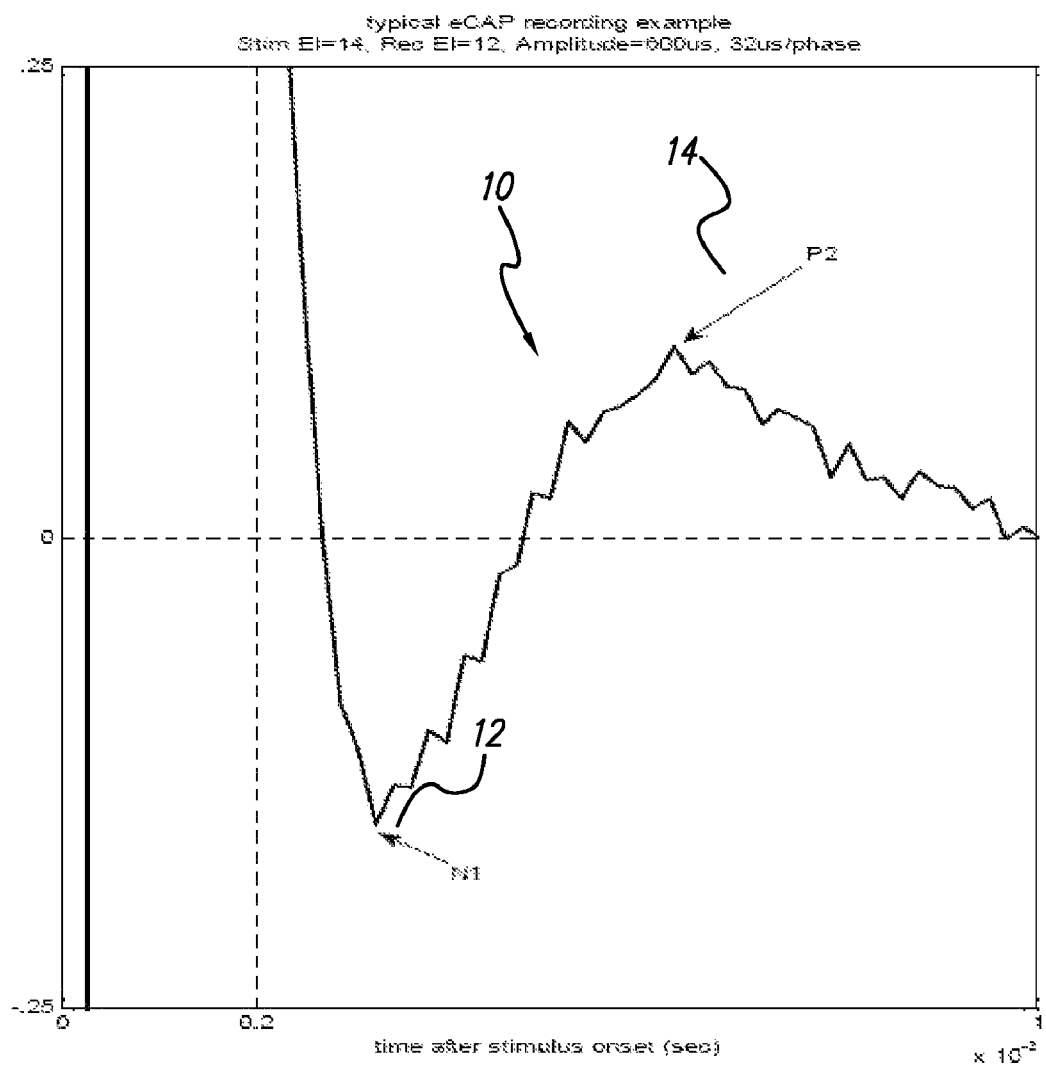
FIG. 1 is a plot of an eCAP recoding collected from a cochlear implant user, where the neural response was elicited by a 32 µs/phase cathodic-first biphasic pulse at 600 µA/phase amplitude (this plot is the result of 10 recordings, averaged to remove uncorrelated noise)

The eCAP artifact is described as follows with reference to FIG. 1, where a typical example of a single eCAP recording 10 in response to a large biphasic pulse is shown. Recording 10 was taken from a patient implanted with a CI, e.g., a HiRes 90K implant (manufactured by Advanced Bionics Corporation, Valencia Calif.) and using a data collection research software such as, e.g., the Bionic Ear Data Collection System (BEDCS) research software (also from Advanced Bionics Corporation). The cathodic-first biphasic pulse that evoked this neural response may be, e.g., amplitude of 600 μA and duration of 32 μs/phase. The plot shown in FIG. 1 is the result of several recordings, e.g., ten recordings averaged to remove uncorrelated noise. Recording 10 demonstrates the typical N1 and P2 aspects of the neural recording shown by arrows 12 and 14. The N1 refers to the first "inverted" depolarization aspect of the compound action potential and P2 is generally described as the refractory aspect of the compound action potential. Previous performed tests demonstrated that the response to the biphasic pulse is located between 100 and 250 μs after the stimulus onset. Therefore in the example shown in FIG. 1, the start of the N1 aspect of the response is difficult to ascertain as it could be obscured by the relatively slow downward decay that appears after the stimulus ends at 64 μs. If the artifact did not exist, the value at 64 μs may be expected to be at the steady state, e.g., −0.25 mV in this example. This decay is caused by the recording artifact whose nature will be analyzed and explained hereinafter.

Figure 2:
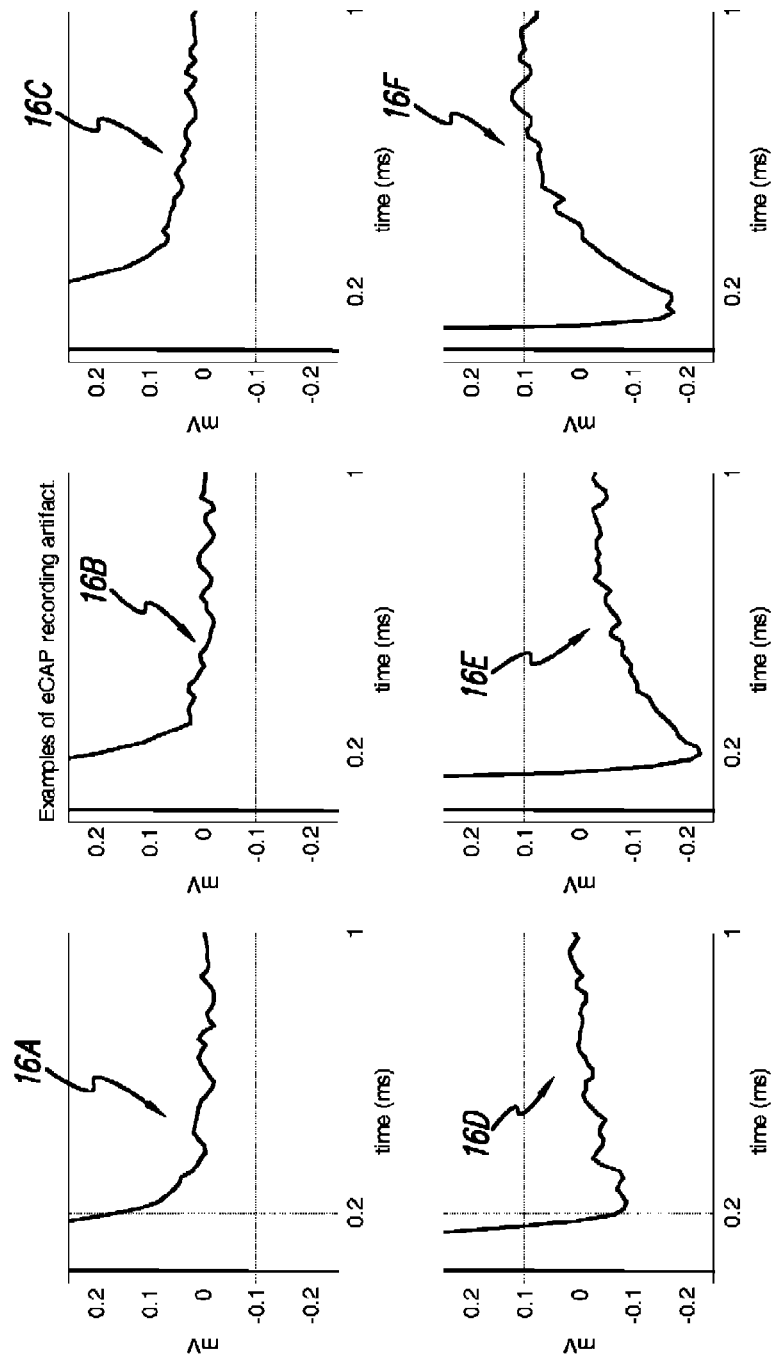
FIG. 2 shows several plots of eCAP recordings collected from several users; the recordings were elicited using a cathodic-first biphasic pulses 32 µs/phase at sub-threshold amplitudes (slow decaying and over-shooting artifacts are evident in these recordings)

A set of typical recordings 16A, 16B, 16C, 16D, 16E, and 16F of the eCAP in response to a biphasic stimulation pulse are shown in FIG. 2. These recordings are examples of sub-threshold recordings that were taken from various patients implanted with a cochlear stimulator, e.g., a HiRes 90K implant. The recordings were made using a Neural Response Imaging (NRI) recording system. (NRI-measurements, are described, e.g., in U.S. Pat. Nos. 6,157,861 and 6,195,585, incorporated herein by reference, and relate, in general, to monitoring a response evoked by application of a stimulus pulse.) The recordings shown in FIG. 2 demonstrate that an artifact can have a slow decay and can overshoot.

Turning now to the electrical-equivalent model 100 shown in FIG. 3, where the model 100 combines ideal hardware components which are used for modeling electrical models of an ideal cochlear implant 20, electrode leads 30, electrode-tissue interfaces 40, and tissue impedances 50. The electrical-equivalent model 100 is intentionally left simple to not include the neural tissue response or the imperfections of implant components. The simulation is designed to emit a biphasic current pulse of 32 μs/phase from the current source 22 termed Src, and then record the response on the recording scope 24. The model 100 is implemented using, e.g., Matlab 7.01 (R14) and Simulink with SimPowerSystems modeling tools and applying the TR-BDF2 ode23tb solver with a relative tolerance of, e.g., $1\,e^{-6}$.

The electrical-equivalent model 100 consists of the ideal current source 22, an ideal amplifier 26, and the coupling capacitors (Cc) referenced as 28-1, 28-2, and 28-3 for each of the electrodes. The coupling capacitors 28-1, 28-2, and 28-3 for example are each 0.1 μF. The stimulation electrode wire 31 at the top of FIG. 3 is connected to the positive side of the ideal current source. The stimulation return electrode wire 32 at the bottom of FIG. 3 is not routed through a coupling capacitor, and constitutes system ground, attached to a large electrode, such as the hermetic case of the implant. The amplifier 26 in the center of the model 100 is an ideal voltage monitor, which is connected on the positive side to the recording electrode 34, and on the negative side to the recording return electrode 36. As is the case for the stimulation return electrode 32, the recording return electrode 36 is expected to be large in area compared to the intra-cochlear electrodes. Unlike the stimulation return electrode 32, the recording return electrode 36 is expected to be isolated from the system ground.

The electrode leads 30 are generally composed of thin metal wire conductors that are embedded in a biocompatible insulating material. The wire conductors are isolated from each other with a polymer coating. The capacitance between individual wires in several electrode leads, e.g., the Hifocus and Helix electrode leads, manufactured by Advanced Bionics of Valencia, Calif., were measured. From the electrode leads tested, the capacitance between the individual electrode wires ranged between 5 and 30 pF with a mean value of 18 pF. The capacitance between the electrode wires and the return electrode ranged between 6 and 12 pF with a mean value of 8 pF. In the model 100 Csr 38 refers to the stimulating-to-recording electrode wire capacitance; Csg 37 refers to the electrode wire to return electrode capacitance for the stimulating electrode; and Crg 39 refers to the electrode wire to return electrode capacitance 27 for the recording electrode.

In order to model the electrode-to-tissue interfaces, general electrical equivalent models described in the following literature were followed:

McAdams, E. T., et al., "*The Linear and Nonlinear Electrical-Properties of the Electrode-Electrolyte Interface*". Biosensors & Bioelectronics, 1995. 10(1-2): p. 67-74.

Brummer, S. B. and M. J. Turner, "*Electrochemical Considerations for Safe Electrical-Stimulation of Nervous-System with Platinum-Electrodes*". IEEE Transactions on Biomedical Engineering, 1977. 24(1): p. 59-63.

Geddes, L. A. and L. E. Baker, *Principles of Applied Biomedical Instrumentation*. 3rd ed. 1989, New York: Wiley. xxvi, p. 961.

The values for the interfaces depend on the ionic concentration of the tissue, electrode material, electrode surface geometry, and frequency. The ranges of values for the interfaces were obtained empirically from patients using for example the Hifocus and Helix electrodes. An electrical field imaging measurement (EFIM) software tool or similar software tool may be used to obtain the estimates of these values. The typical ranges for these values are identified in table 200 shown in FIG. 4. The table 200 shows ranges of relevant values 206 used in the eCAP recording electrical-equivalent model 100. The nominal parameter values 208 are chosen as the mean of each range. Each of these values, the relevant values 206 and the nominal values 208 correspond to a specific parameter description 204. Each parameter description 204 is defined by a parameter name 202. Each parameter name 202 is also shown in model 100.

All simulations are conducted using the ideal current source 22 at the top left part of electrical-equivalent model 100 shown in FIG. 3. During simulations, the current source 22 emits a biphasic current pulse, with a duration of 32 μs/phase and amplitude of 300 μA/phase. After the end of the biphasic pulse, the current source 22 is left as an open circuit. Since the nature of the eCAP response demands that the artifact is negligible starting at, e.g., 200 μs, observations are concentrated on the resulting measurement from the Amp to the first 1 ms. Also, since the eCAP recording is on the order of several hundred μV in amplitude, the voltage observations are limited to the window of ±250 μV.

Figure 5:
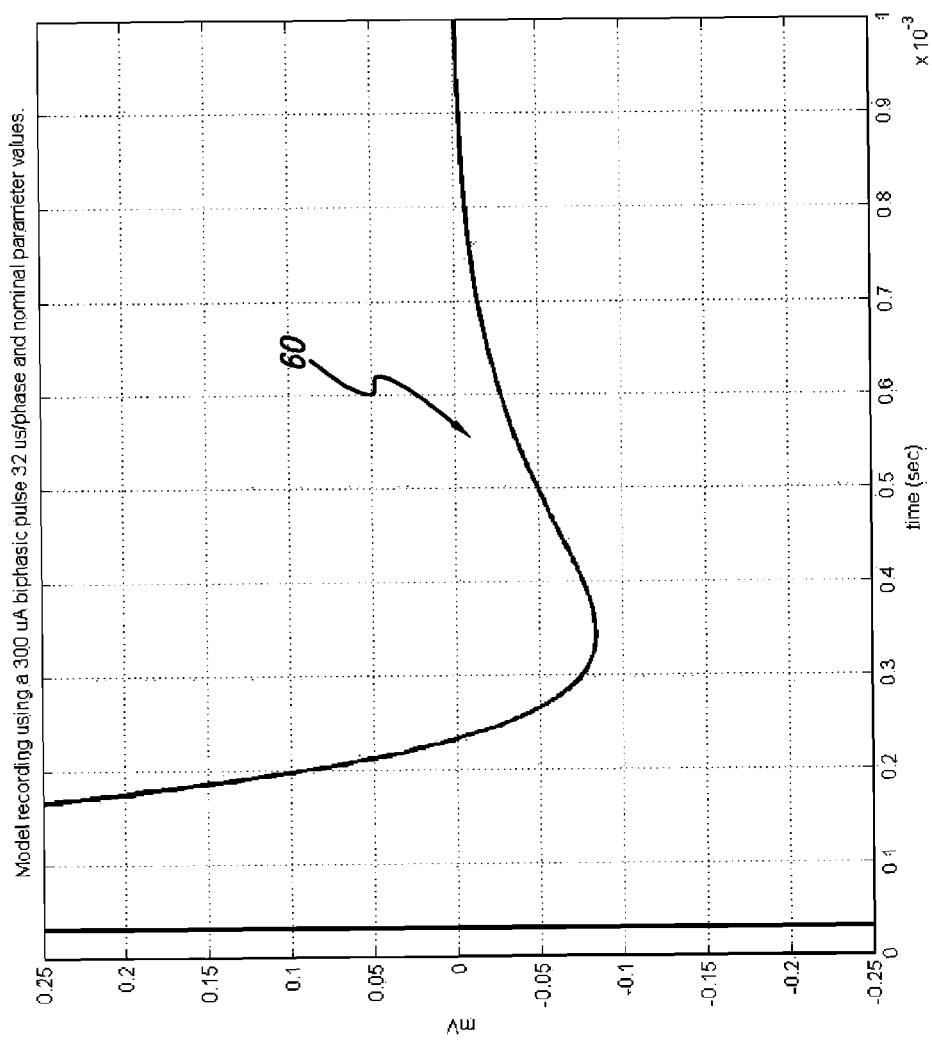
FIG. 5 is a plot of an eCAP measurement evoked using the electrical-equivalent model simulating a 300 µA/phase amplitude at 32 µs/phase biphasic pulse and using the nominal parameter values from the table shown in FIG. 4.
Figure 6:
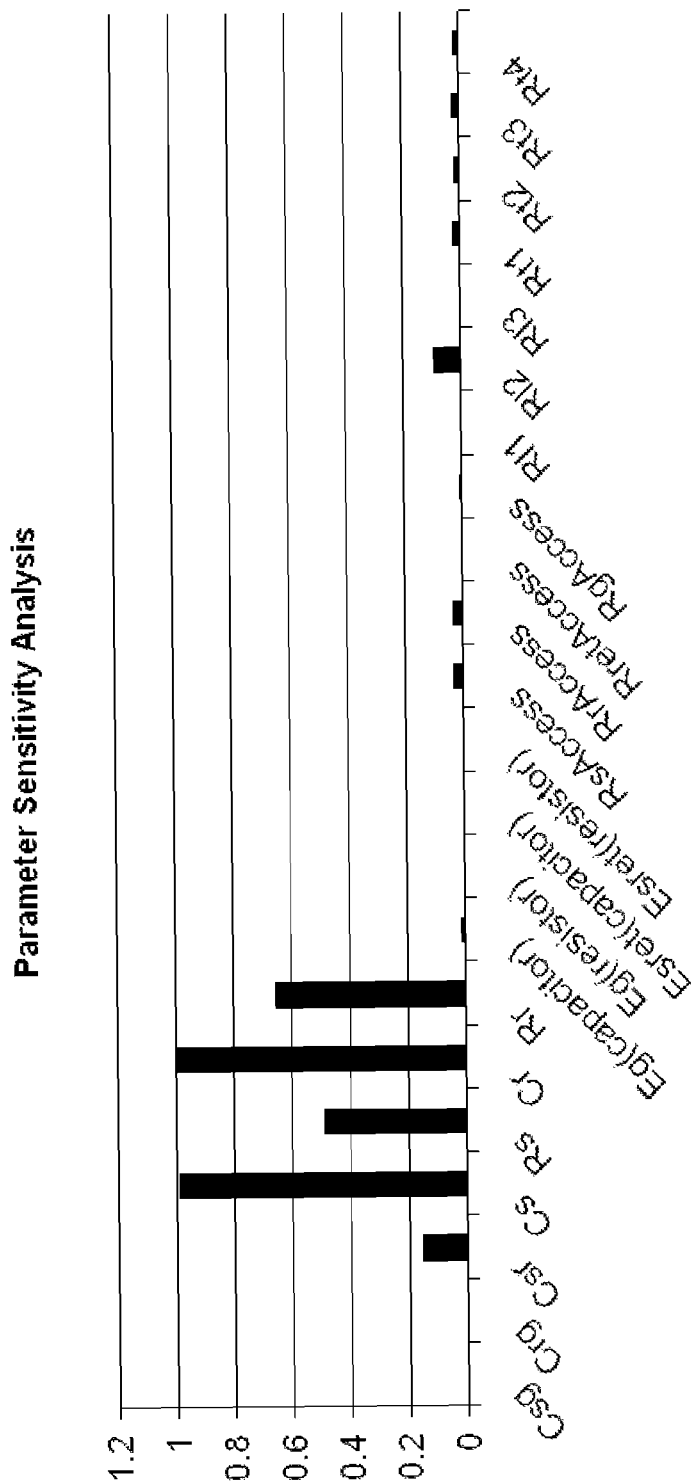
FIG. 6 is a comparison plot showing the eCAP artifact sensitivity measured as the deviation from the artifact obtained with the nominal eCAP recording values, where the measures of sensitivity were obtained as a mean-squared error between the model eCAP recording obtained by varying an individual parameter and the nominal value (values shown in FIG. 6 have been scaled to produce the comparison plot)

The Parameter Sensitivity and Output of the electrical-equivalent model 100 will next be described. The sensitivity of the electrical-equivalent model 100 is estimated to various parameter perturbations. Each nominal parameter value 208 was varied to the highest and the lowest values in its range. For each parameter 208 the mean squared error was calculated between the recording obtained from varying that parameter and the nominal recording plot 60 is obtained, as shown FIG. 5. The lack of the artifact would have resulted in a horizontal line at 0 mV after 64 μs. The mean squared errors due to varying each parameter are compared in FIG. 6. The parameters which have the largest effect on the overall recording are the electrode-to-electrode parasitic capacitance Csr, electrode surface characteristics (Cs, Rs, Cr, and Rr), and the longitudinal resistance between the recording return electrode and the recording electrode R12, all shown in FIG. 6.

Figure 7:
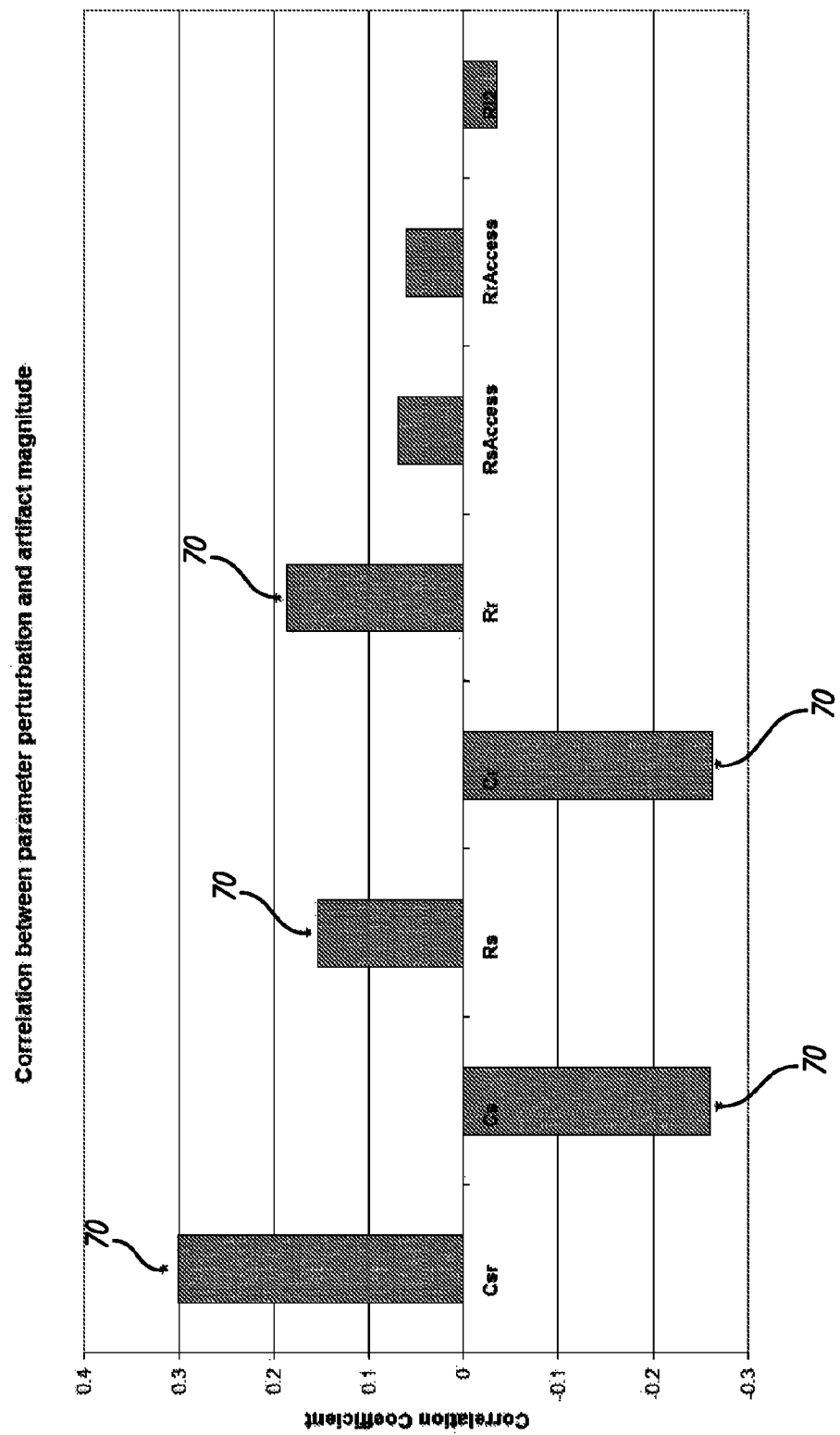
FIG. 7 is a plot showing the correlation between the magnitude of the artifact and the manipulation of the sensitive parameter values, where the correlations shown indicate that the artifact magnitude increases with increasing resistance and decreasing capacitance across electrode contact wires.

The model recordings were obtained with respect to every permutation of the most sensitive parameters as each parameter varied between its maximum and minimum values. The artifact was measured as the mean squared error between a flat line at 0 mV and each recorded trace. The correlations between the artifact and the parameter values are plotted in FIG. 7. The asterisks 70 indicate the statistically significant contributions from the various parameters ($p<0.05$). This plot suggests that the artifact increases with respect to increased parasitic capacitance between stimulating electrode and recording electrode, Csr 38. It also indicates that the artifact becomes larger as the electrode impedance increases, as indicated by the positive correlation with the electrode resistance and the negative correlation with the electrode capacitance. The increase in the magnitude of the artifact with respect to impedance is consistent. An implant making an eCAP measurement in phosphate buffered saline (PBS) contains no artifact, however, once the saline is diluted to the point at which the electrode impedances match those of patients, the artifact, similar to the patients' artifact appears.

Figure 8:
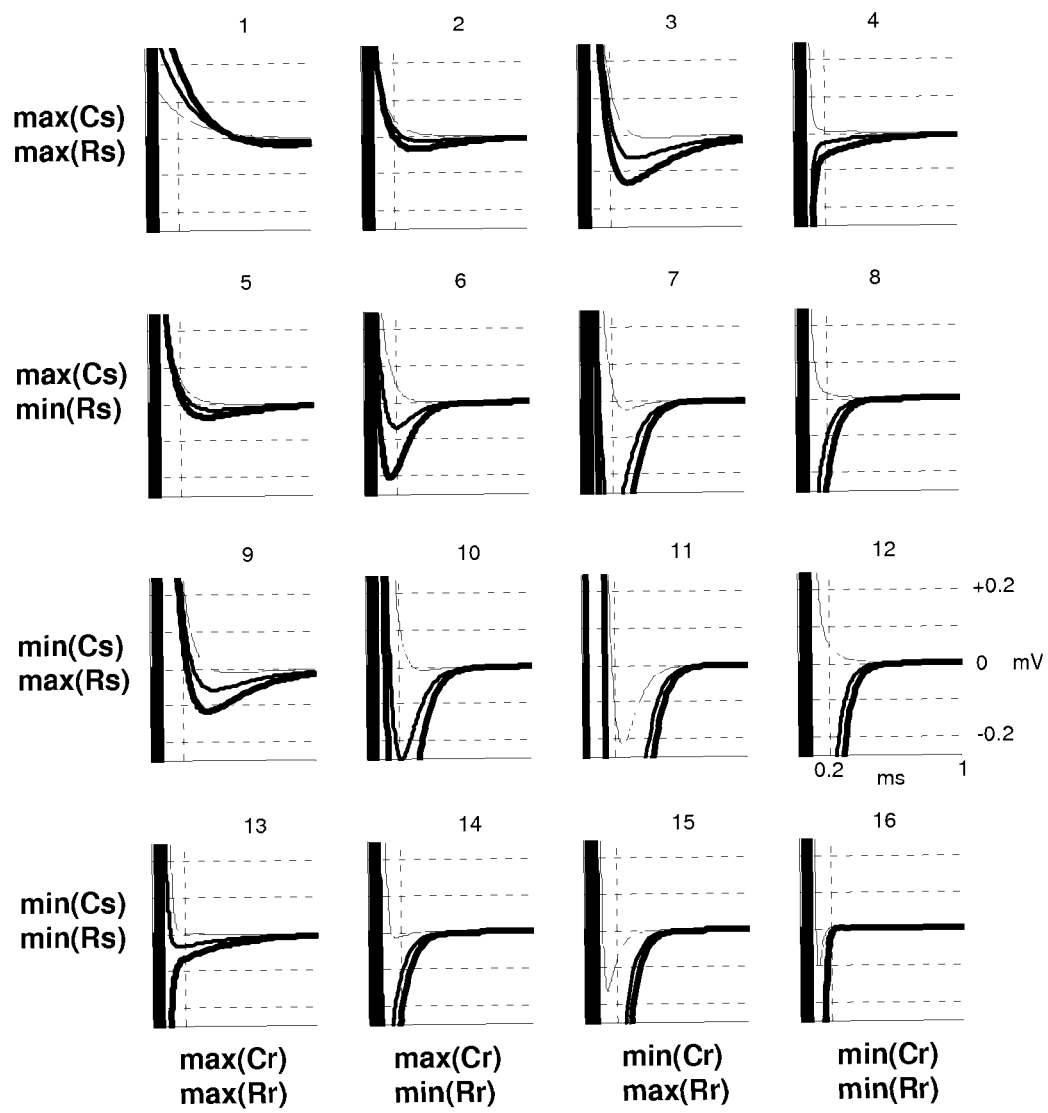
FIG. 8 depicts sixteen plots showing varying artifact trajectories recorded from the electrical-equivalent model shown in FIG. 3.

To further understand the behavior of the eCAP recording artifact in the model 100, the model outputs are observed as the characteristics of the electrode surface are varied, where FIG. 8 shows artifact trajectories 1-16 recorded from the model. The plots 1-16 vary in their recording electrode characteristics along the horizontal axis, and in their stimulating electrode characteristics along the vertical axis. Line thickness indicates the value of the parasitic electrode-to-electrode capacitance Csr 38, in order of value, so that the minimum value is indicated by the thinnest line, and the maximum value is indicated by the thickest line. As in real patient recordings, a full range of artifacts are possible from artifacts that decay slowly, to ones that overshoot. In general, the thin lines exhibit the smallest artifact in each plot, suggesting that the artifact magnitude is strongly correlated to the parasitic capacitance between electrodes. These recordings further suggest that the artifact dynamics are the result of interplay between stimulating and recording electrode interfaces, interacting through the parasitic coupling between the electrode wires.

The plots 1-16 shown in FIG. 8 also show the effect of different parasitic capacitances between stimulating and recording electrodes, indicated by trace thicknesses. Thin traces indicate the system output as the low parasitic inter-electrode coupling is used, and the thick traces are the result of high inter-electrode coupling. This coupling is the Csr 38 parameter. In the case of low parasitic capacitance, this parameter is set to 6 pF, in the case of medium coupling, it is set to 18 pF, and in the case of high coupling, the value is set to 30 pF.

One interesting feature of this analysis is that both a slow decay and an overshoot are possible in this system, just as in the actual recording shown in FIG. 2. Another observation is that the electrode interface impedance values have little effect on the artifact when the electrode parasitic capacitance is small, as shown by the thin traces.

Model Analysis and Artifact Explanation

Figure 9:
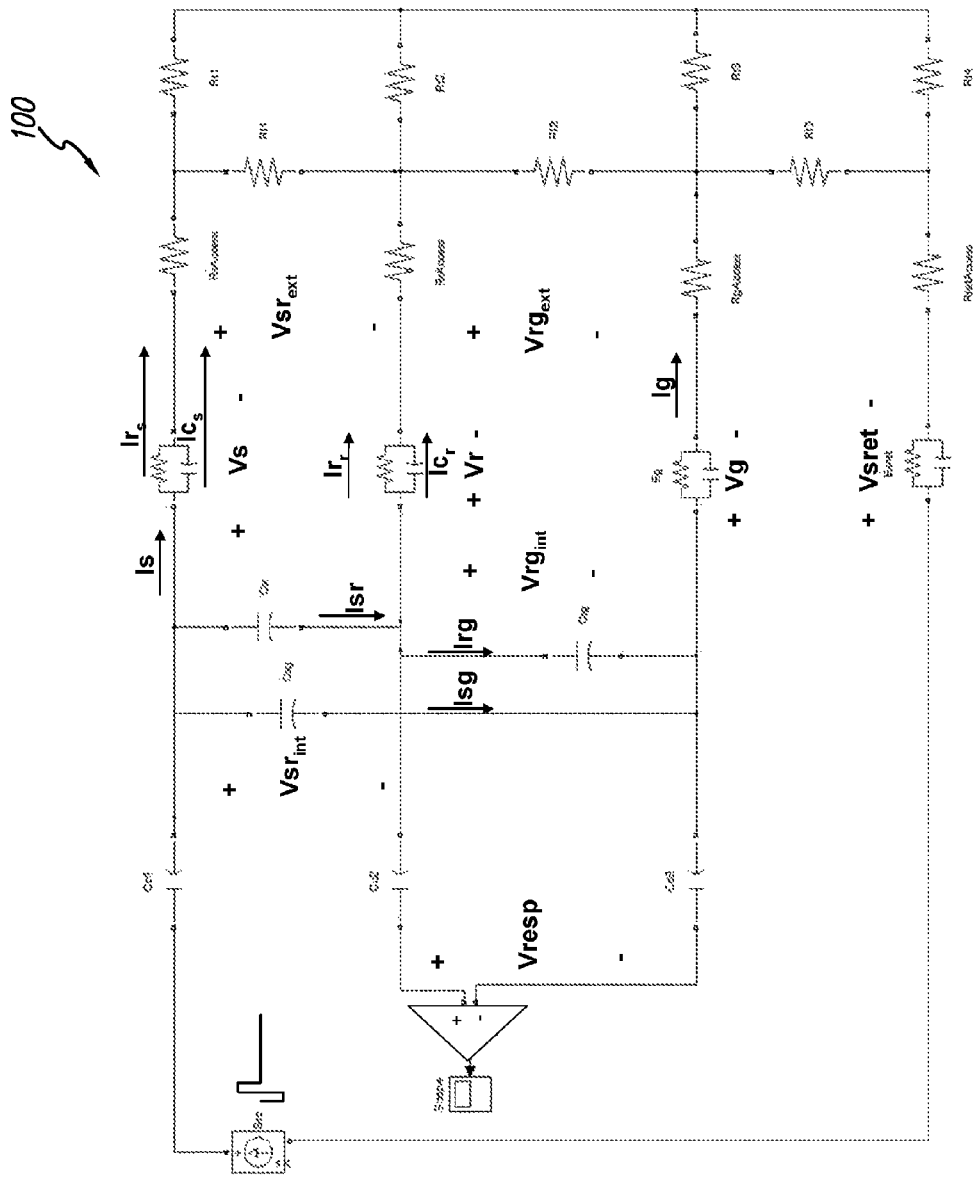
FIG. 9 is the electrical-equivalent model shown in FIG. 3 with voltage and current directions defined.

An electric analysis of the model is conducted, where the main components in the model which are responsible for the artifact are identified in FIG. 9. Measurements for the model are also defined in FIG. 9. The nominal parameter values 208, shown in FIG. 4, are used for this analysis. The current source 22 is set to provide a biphasic pulse of 32 μs/phase and 300 μA/phase.

Figure 10:
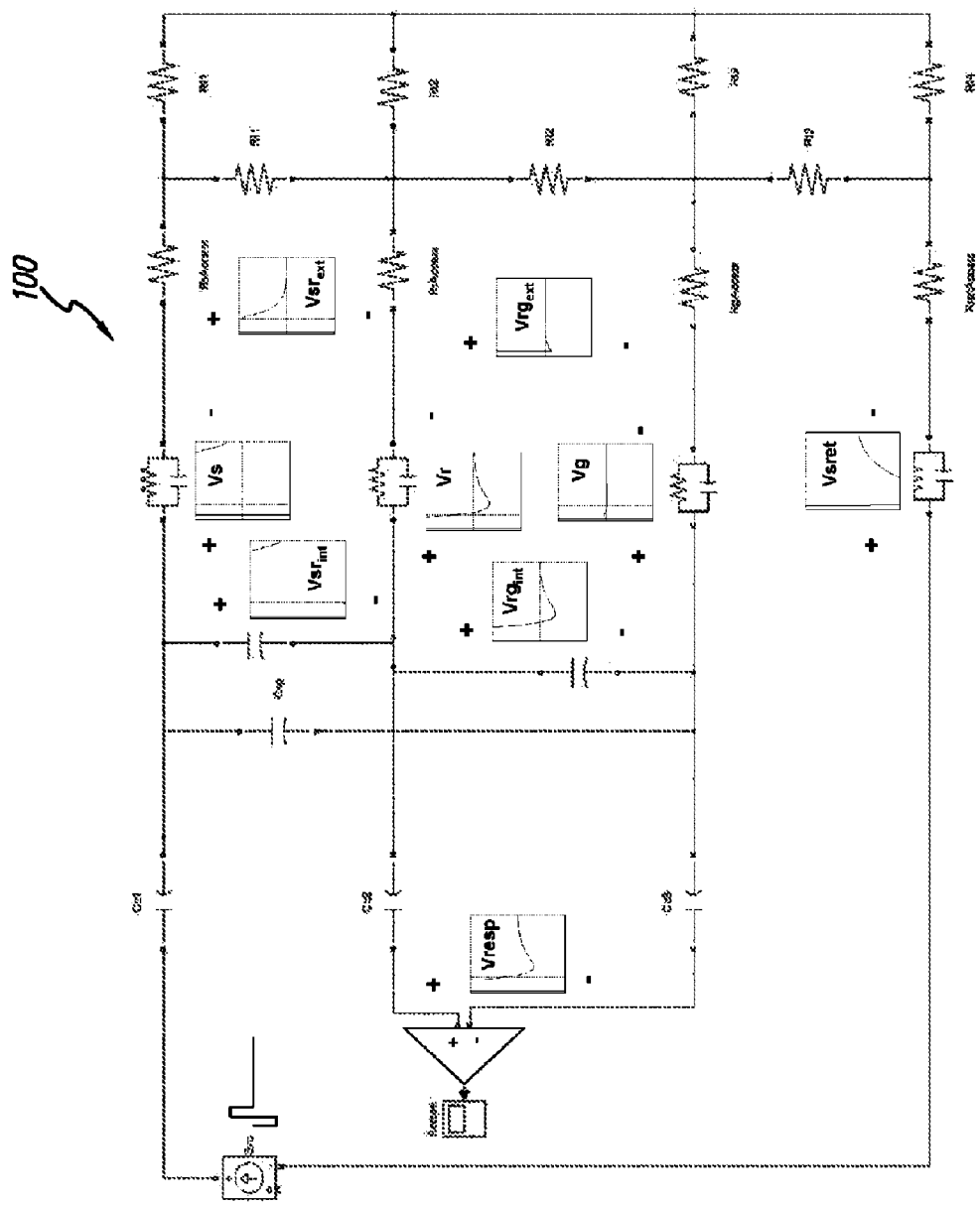
FIG. 10 is the electrical-equivalent model shown in FIG. 3 showing recordings for the voltage measurements (for each measurement, the X-axis is from 0 to 1 ms long and contains a dashed line at 200 µs and the Y-axis is from −250 to +250 mV with a dashed line at 0)

FIG. 10 shows the voltages relevant to the artifact. Vresp is the response recorded by the implant. Since the input impedance of an ideal amplifier is infinite, it can be seen that Vint will be exactly equal to Vresp. By Kirchhoff's law, the sum of all voltages in any loop of a circuit must equal to zero (0). Therefore $Vrg_{int}$ is the sum of Vr, $Vrg_{ext}$, and Vg. From measuring these voltages we see that Vr provides by far the most significant contribution to the recorded artifact.

From FIG. 10, stimulation is a cathodic-first biphasic pulse 32 μs/phase, 300 μA/phase. For each measurement, the X-axis is from 0 to 1 ms long and contains a dashed line at 200 μs. The Y-axis is from −250 to +250 mV with a dashed line at 0. The polarity in each plot is as indicated with the convention of positive at top or left of each plot. The artifact voltage trace Vresp is nearly equivalent to the voltage across the recording electrode Vr. The voltages immediately following the stimulation pulse, at 64 μs indicate the large positive charge stored across the stimulating electrode, and a smaller positive charge stored across the recording electrode. The implication is that the biphasic stimulation current leaks through the parasitic capacitance Csr, and causes the charging across the recording electrode. The dissipation of the charges stored across the stimulating and recording electrodes appear to be the cause of the artifact trajectory following the stimulation pulse.

Immediately after the stimulation pulse is completed, at 64 μs, a very large voltage, Vs, across the stimulating electrode is observed, and a small, but not insignificant voltage, Vr, across the recording electrode is also observed. In FIG. 10, these values are off the scale, but their magnitude can be inferred from the plots.

The observation that the voltage trace Vr, measured across the recording electrode is the same as the system response voltage Vresp, suggests that a closer look at the dynamics occurring at the recording electrode interface should be emphasized.

Figure 11:
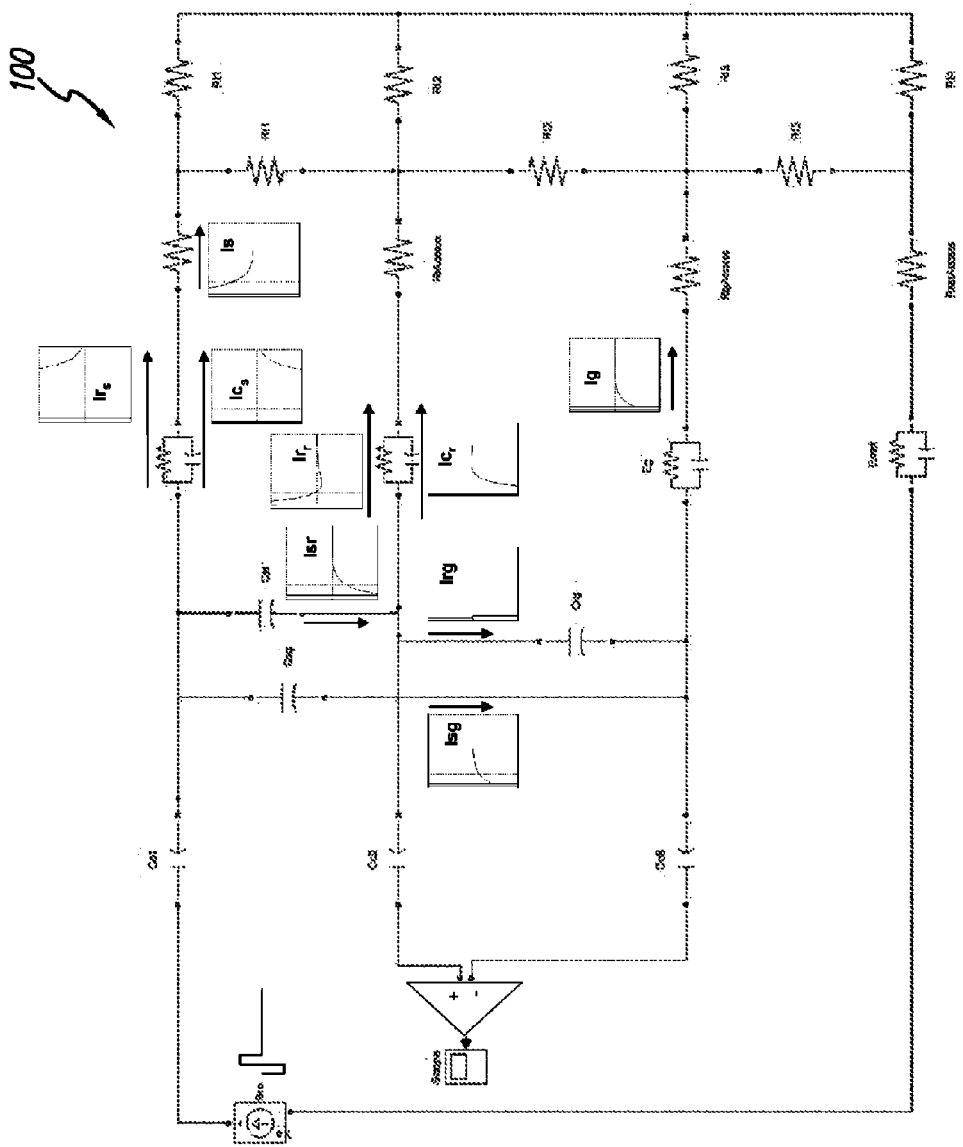
FIG. 11 is the electrical-equivalent model shown in FIG. 3 showing recordings for the current measurements (for each measurement, the X-axis is from 0 to 1 ms long and contains a dashed line at 200 µs and the Y-axis is from −50 to +50 nA with a dashed line at 0)

FIG. 11 shows the recording of the current measurements using the eCAP electrical-equivalent model 100. Stimulation is a cathodic-first biphasic pulse 32 μs/phase, 300 μA/phase. For each measurement, the X-axis is from 0 to 1 ms long and contains a dashed line at 200 μs. The Y-axis is from −50 to +50 nA with a dashed line at 0. The direction of current is as indicated with the convention of downward or to the right on each plot. The charge collected across the stimulation interface capacitance Cs, is dissipating primarily through the interface resistance ($Ir_s$), and through the tissue resistance RsAccess (Is). The dynamics of the artifact are due to interactions between $Ic_r$, $Ir_r$, and Isr.

The qualitative interpretation of the resulting currents is that the large charge stored at the stimulating interface, Vs at 64 μs, after the completion of the pulse, is discharging through two current paths: $Ir_s$ and Is where Is enters two current loops: one that comes back through the recording electrode, indicated by Isr, and one that comes back through the recording return electrode, indicated by Ig and then Isg. The current across the recording electrode causes a voltage change across the recording electrode, proportional to the recording electrode impedance. However, since some voltage is already stored at the recording electrode as the result of the stimulation pulse, the dynamics of Vr are complicated by the draining of that small charge across the resistive path of the recording electrode, $Ir_r$.

The implication is that the stimulating electrode and the recording electrode interfaces get charged during the stimulation delivery, and the decay of this charge is seen as the artifact at the amplifier.

Artifact Solution Suggested by the Model

As shown above, the eCAP artifact appears to be caused primarily by the draining of the charges accumulated at the stimulating and recording electrodes through the inter-electrode-wire parasitic capacitance. If it was possible to not accumulate the charge at the electrodes in the process of stimulation, there would be no artifact due to the discharge at the electrode interfaces.

Figure 12A:
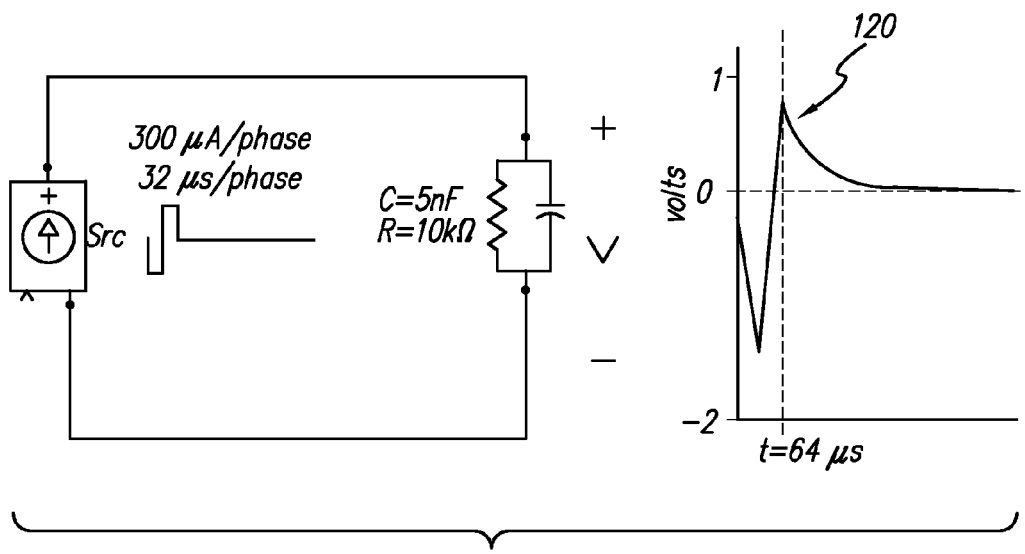
FIG. 12A is a schematic of a parallel resistor-capacitor pair and associated plot showing a balanced biphasic pulse indicating that a charge at the electrode interface in deposited, which charge slowly decays after the current pulse is completed.
Figure 12B:
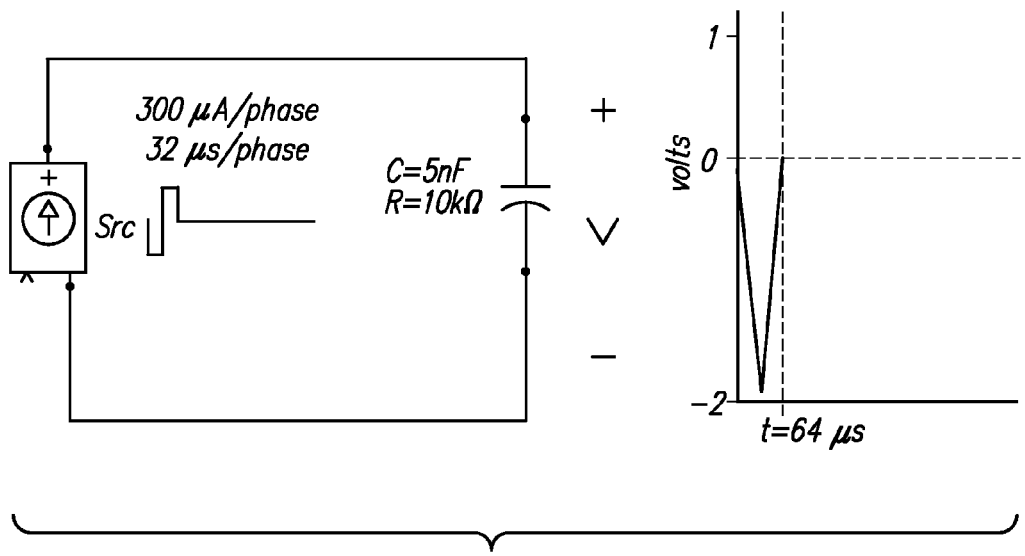
FIG. 12B is a schematic of a perfect capacitor and associated plot showing that the charge will accumulate across the capacitor on the negative phase of the current pulse and will be dissipated precisely in the opposite direction by the positive phase.

The reason that a charge remains at the electrode interface after a perfectly balanced current pulse is delivered is due entirely to the Faradaic (resistive) component of the electrode interface. This is demonstrated in FIGS. 12A and 12B. The charge is left across the capacitor in the case of the parallel resistor-capacitor pair, shown in FIG. 12A. This is because during the negative phase of the current pulse, as the charge is accumulated across the capacitor, some of this charge leaks through the resistor. However, since the positive phase of the biphasic pulse is as large as the negative, the voltage across the capacitor does not simply return to the original zero, but instead, an overshoots 120 occurs and then slowly drains through the resistor after the pulse is completed. In the case of a perfect capacitor, as shown in FIG. 12B, the charge will accumulate across the capacitor on the negative phase of the current pulse and will be dissipated precisely in the opposite direction by the positive phase. A perfectly balanced biphasic pulse will deposit charge at the electrode interface, which will slowly decay after the current pulse is completed, as indicated by the plot shown in FIG. 12A. In the case of an ideal capacitive interface, there will be no remaining charge after the biphasic pulse, as indicated in the graph shown in FIG. 12B. Therefore, using capacitive electrodes in a neural stimulator, e.g., cochlear implant, would eliminate the eCAP artifact.

There have been a number of proposals in the literature with respect to creating capacitive electrodes for neural stimulation [Rose, T. L., E. M. Kelliher, and L. S. Robblee, "*Assessment of Capacitor Electrodes for Intracortical Neural Stimulation*". Journal of Neuroscience Methods, 1985. 12(3): p. 181-193; Loeb, G. E., et al., "*Injectable Microstimulator for Functional Electrical-Stimulation*" Medical & Biological Engineering & Computing, 1991. 29(6): p. NS13-NS19; and U.S. Pat. No. 5,833,714, entitled: "Cochlear Electrode Array Employing Tantalum Metal.", where the articles and the patent are all incorporated by reference.] The primary reason for this effort is to increase the electrode safety. The other reason is to eliminate the need for DC coupling capacitors in the implant and therefore decreasing the implant size. A comparison of various capacitive electrodes can be found in [Rose, T. L., E. M. Kelliher, and L. S. Robblee, p. 181-193]. From this reference, the typical cochlear implant electrode size of 0.2 mm², a Titanium Oxide film coated electrode would have approximate capacitance of 30 nF and resistance of 1500 MΩ.

Figure 13:
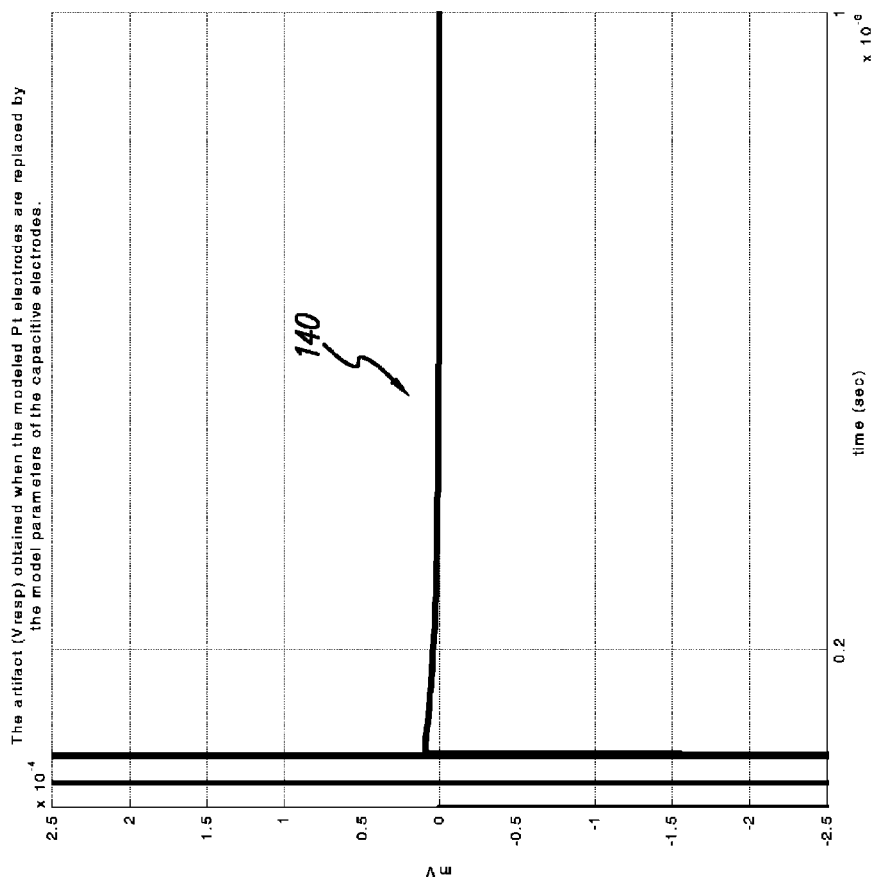
FIG. 13 is a plot showing an eCAP recording when the electrode parameters are replaced from a more Faradaic material, e.g., Pt electrodes, with parameters from pure capacitive materials, e.g., $Ta_2O_5$, $TiO_2$, or similar compounds, or other dielectric coatings or films.

When the stimulating and recording electrodes are set to capacitive electrode parameter values using model 100, that is when the electrodes having a more Faradaic material, e.g., Pt electrodes, are replaced with parameters of capacitive electrodes, e.g., $Ti_2O_5$, $TiO_2$, or other dielectric coatings or films, the resulted plot 140 shown in FIG. 13 is obtained. In plot 140 the capacitive and resistive values were set, e.g., Cs=Cr=29.6 nF and Rs=Rr=1.5 $e^9$Ω. In further model manipulations, it was discovered that increasing the interface resistance to Rr=Rs=5 MΩ was sufficient to suppress the artifact to below 50 μV in the worst possible case of min Cs and min Cr, as shown in FIG. 11. The value of 5 MΩ is still significantly lower than the highest DC leakage resistance of 7.8 MΩ) calculated for a worst-case capacitive electrode [Rose, T. L., E. M. Kelliher, and L. S. Robblee, p. 181-193]. Thus, the results presented herein suggest the use of capacitive electrodes to remove the eCAP artifact.

As described above, the eCAP recording artifact is shown to be directly linked to the parasitic capacitance between electrode wires inside the cochlear electrode lead, and the electrode-tissue interface electro-chemical characteristics. The charge is accumulated at the electrode-tissue interface on the stimulating electrode, and through the parasitic capacitive leakage, at the recording electrode. The dissipation of the charge stored at these two electrodes is seen as the artifact at the amplifier. Since the parasitic capacitance between electrode wires is not generally controlled during the manufacturing process, it could account for the unreliable nature of the artifact.

The difficulty of validating this theoretical treatment of the artifact lies in obtaining a perfect characterization of the implant, the electrode capacitances prior to implantation, and an accurate model of the electrode-tissue interface once the electrode has been implanted.

Some validation that the eCAP artifact is the result of electrical and electrode-impedance characteristics and not due to biological effects will be explained next. A cochlear implant and electrode is immersed in a diluted phosphate buffered saline (PBS) solution. PBS was diluted with distilled water to the point at which the impedances matched those in a typical patient. A number of eCAP recordings were then collected. These recordings contained eCAP artifacts that are typically seen in patients. Furthermore, in several instances there was a correlation between the parasitic capacitance between electrode wires and the amplitude of the artifact.

The addition of the electrode and tissue model to a realistic cochlear implant model, e.g., Advanced Bionics cochlear implant ASIC model using Mentor Graphics software, further confirmed that the artifact is caused by the accumulation of charge at the stimulation electrode interface. The dissipation of that charge caused the artifact in this realistic hardware model as well. However, the charge dissipation path that caused the artifact, was not dominated by the inter-electrode capacitances. In this more realistic model, the charge accumulated at the stimulation electrode was dissipated primarily through the recording ground electrode coupled to the system ground. This current flow caused a potential to be generated between the recording electrode and the recording ground.

In both the ideal case and our more realistic model, for example using the implant ASIC simulation Mentor Graphics tool, the primary cause of the artifact was the charge stored at the electrode-tissue interfaces. Leaking this left-over electrode-interface charge through the unintended current paths creates potentials in the system, which are seen by the recording amplifier. These unintended current paths include the parasitic coupling between electrodes as well as the parasitic capacitances to ground, internal to the implant.

The solution to the artifact problem consists of changing the electrode technology from Faradaic electrodes, typically Pt or Pt—Ir alloy to a capacitive technology. A number of capacitive electrodes have been proposed in the known technology, e.g., U.S. Pat. No. 5,833,714, previously incorporated herein by reference, for the purpose of safety. The known technologies include using, e.g., Tantalum Pentoxide ($Ta_2O_5$), Titanium Oxide ($TiO_2$), and using various coatings, such as Titanium Nitride (TiN) and Barium Titanate (Ba-$TiO_3$). With the current technological direction in utilizing Micro-Electro-Mechanical Systems (MEMS) to manufacture electrodes [Janders M., E. U., Stelzle M., Nisch W., *Novel Thin Film Titanium Nitride Micro-Electrode With Excellent Charge Transfer Capability for Cell Stimulation and Sensing Applications*. in 18*th Annual International Conference of the IEEE Engineering in Medicine and Biology Society*. 1996. Amsterdam], thin-film and capacitive electrodes are becoming a feasible solution for the purposes of safety, size considerations, and now eCAP recording artifact removal. MEMS is known as the integration of mechanical elements, sensors, actuators, and electronics on a common silicon substrate through microfabrication.

While the techniques herein disclosed have been described by means of specific embodiments and applications thereof, numerous modifications and variations could be made thereto by those skilled in the art without departing from the scope of the invention set forth in the claims.

What is claimed is:

1. A system for measuring an evoked compound action potential (eCAP) artifact, the system comprising:
    an electrical-equivalent model, wherein in the model includes an ideal current source having a positive and negative side; a stimulation electrode coupled to the positive side of the current source through a first coupling capacitor; a large electrode, comprising a system ground, connected to the negative side of the current source without being routed through a coupling capacitor; an ideal amplifier having a positive side and a negative side; a recording electrode coupled to the positive side of the ideal amplifier through a second coupling capacitor; and a recording return electrode coupled to the negative side of the amplifier through a third coupling capacitor; and
    means for recording a voltage artifact at the recording electrode;
    wherein the electrical-equivalent model is configured to emit a biphasic current pulse from the current source and apply the biphasic current pulse to the stimulation electrode, and wherein the current source is left as an open circuit after the end of the biphasic current pulse, and wherein the means for recording measures the eCAP artifact appearing at the recording electrode after a response time.

2. The system of claim 1 wherein the recording return electrode is isolated from the system ground.

3. The system of claim 1 wherein the electrical equivalent model further includes at least one electrode-tissue interface model that simulates respective electrical connections between the first, second and third coupling capacitors and the stimulation electrode, recording electrode and recording return electrode, and between the negative side of the current source and the stimulation return electrode, and wherein the electrode-tissue interface model comprises a parallel capacitor-resistor pair in series with an access resistor.

4. The system of claim 1 wherein the electrical equivalent model further includes at least one tissue impedance model that simulates the interface between the electrodes and tissue, wherein the tissue impedance model comprises a resistor-ladder network.

5. The system of claim 1 wherein the electrical equivalent model further includes at least one electrode lead model that simulates an electrical lead connecting the coupling capacitors and negative side of the current source with the electrodes, wherein the electrode lead model comprises a cross-wire parasitic capacitor.

6. The system of claim 1 wherein the biphasic current pulse emitted by the ideal current source comprises a pulse that is 32 µs/phase and 300 µA/phase.

7. An electrical-equivalent model configured to record an evoked compound action potential (eCAP) artifact, the model comprising:
    a neural stimulator portion, said stimulator portion including an ideal current source;
    an electrode lead portion;
    an electrode interface portion;
    a tissue interface portion; and
    means for recording an eCAP artifact;
    wherein the portions are coupled to simulate a biphasic current pulse emitted from the current source and applied to stimulation electrodes in the electrode interface portion, and wherein the current source is left as an open circuit after the end of the biphasic current pulse, and wherein the means for recording measures the eCAP artifact after a time response, wherein the eCAP artifact is measured at recording electrodes in the electrode interface portion in response to the biphasic current pulse being applied to the stimulation electrodes.

8. The model of claim 7 wherein the neural stimulator portion further includes an ideal amplifier, wherein the ideal amplifier is an ideal voltage monitor having a positive side and a negative side, wherein the positive side of the voltage monitor is connected to a recording electrode located in the electrode interface portion and the negative side is connected to a recording return electrode located in the electrode interface portion, and wherein the respective connections to the electrodes is each routed through a respective coupling capacitor.

9. The model of claim 8 wherein the ideal current source in the neural stimulator portion has a positive side and a negative side, and further wherein the electrode interface portion has a stimulating electrode connected to the positive side of the ideal current source through a connection that is routed through the electrode lead portion and through a coupling capacitor.

10. The model of claim 9 wherein the electrode lead portion comprises at least one cross-wire parasitic capacitor, wherein each cross-wire parasitic capacitor is connected to at least one of the coupling capacitors.

11. The model of claim 10 wherein the electrode interface portion comprises at least one capacitor-resistor pair arranged in parallel, wherein each capacitor-resistor pair is connected to at least one of the cross-wire parasitic capacitors.

12. The model of claim 11 wherein the tissue interface portion comprises at least one resistor-ladder network, wherein each of the resistor ladder networks is connected to at least one of the capacitor-resistor pairs.

* * * * *